United States Patent [19]

Heinig et al.

[11] Patent Number: 4,887,595
[45] Date of Patent: Dec. 19, 1989

[54] SURGICALLY IMPLANTABLE DEVICE FOR SPINAL COLUMNS

[75] Inventors: Charles F. Heinig, Charlotte, N.C.; Marc A. Asher, Prairie Village, Kans.; Walter E. Strippgen, Golden, Colo.

[73] Assignee: AcroMed Corporation, Cleveland, Ohio

[21] Appl. No.: 79,457

[22] Filed: Jul. 29, 1987

[51] Int. Cl.$^4$ .................................................. A61F 5/04
[52] U.S. Cl. ........................................ 606/61; 606/72; 606/73
[58] Field of Search ................... 128/69, 92 R, 92 YF, 128/92 YM

[56] References Cited

U.S. PATENT DOCUMENTS

| | | | |
|---|---|---|---|
| 2,494,229 | 1/1950 | Collison | 128/92 YF |
| 3,242,922 | 3/1966 | Thomas | 128/92 YM |
| 4,382,438 | 5/1983 | Jacobs | 128/69 |
| 4,653,481 | 3/1987 | Howland et al. | 128/69 |
| 4,655,199 | 4/1987 | Steffee | 128/69 |
| 4,773,402 | 9/1988 | Asher et al. | 128/69 |

FOREIGN PATENT DOCUMENTS 2289164  5/1976  France .................................. 128/69

Primary Examiner—Edgar S. Burr
Assistant Examiner—Moshe I. Cohen
Attorney, Agent, or Firm—Tarolli, Sundheim & Covell

[57] ABSTRACT

A surgically implantable device for maintaining the relative positions of spinal bodies of a spinal column. The device comprises a plate portion for connection with a first spinal body. The plate portion has a first major side surface for facing the first spinal body and a second major side surface. The plate portion has an opening which extends through the first and second major side surfaces for receiving a fastener to connect the plate portion with the first spinal body. A rod portion is fixedly connected to the plate portion and extends therefrom. The rod portion is bendable to conform to a desired spinal curvature. The rod portion has a part for connection with a second spinal body.

7 Claims, 5 Drawing Sheets

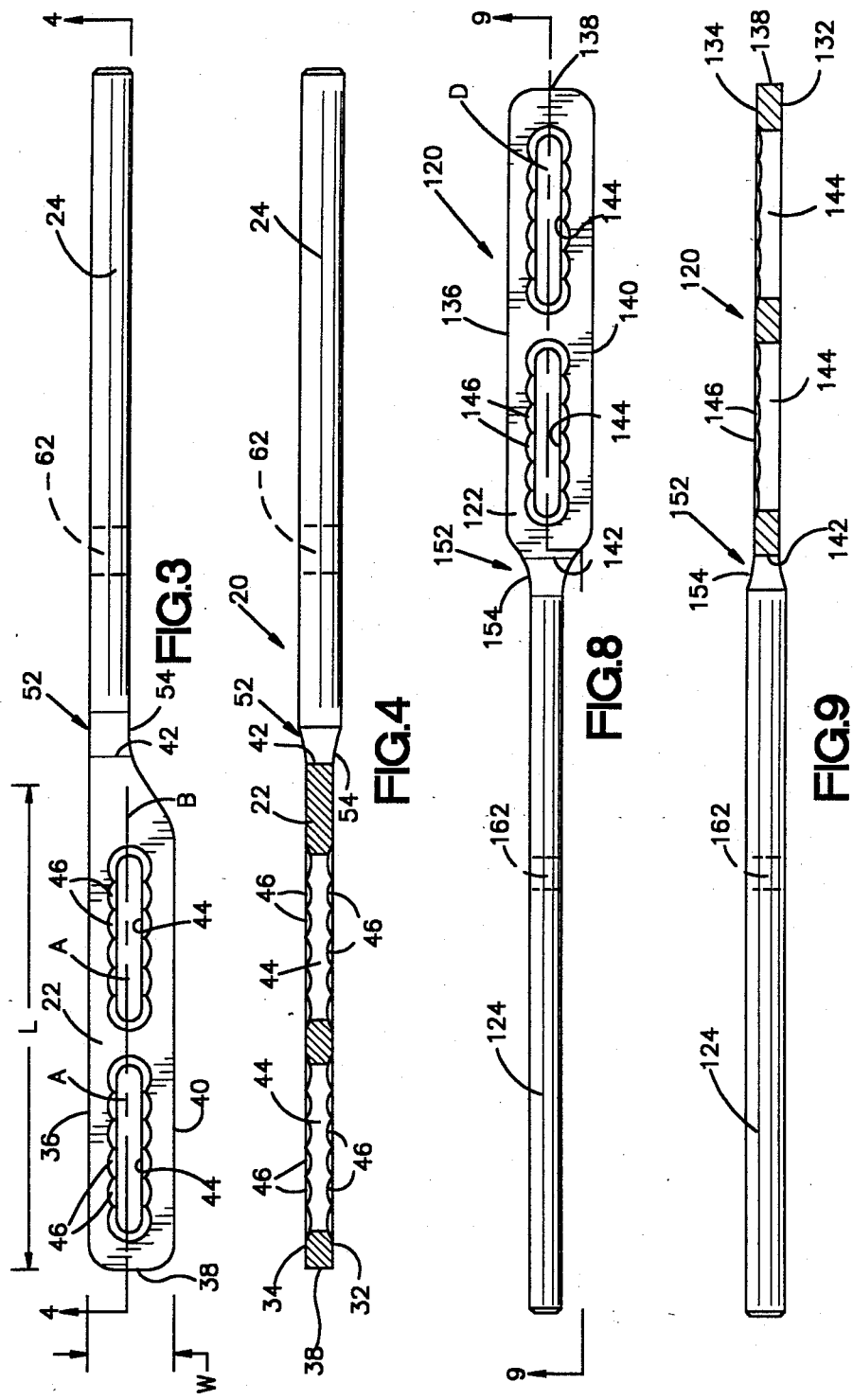

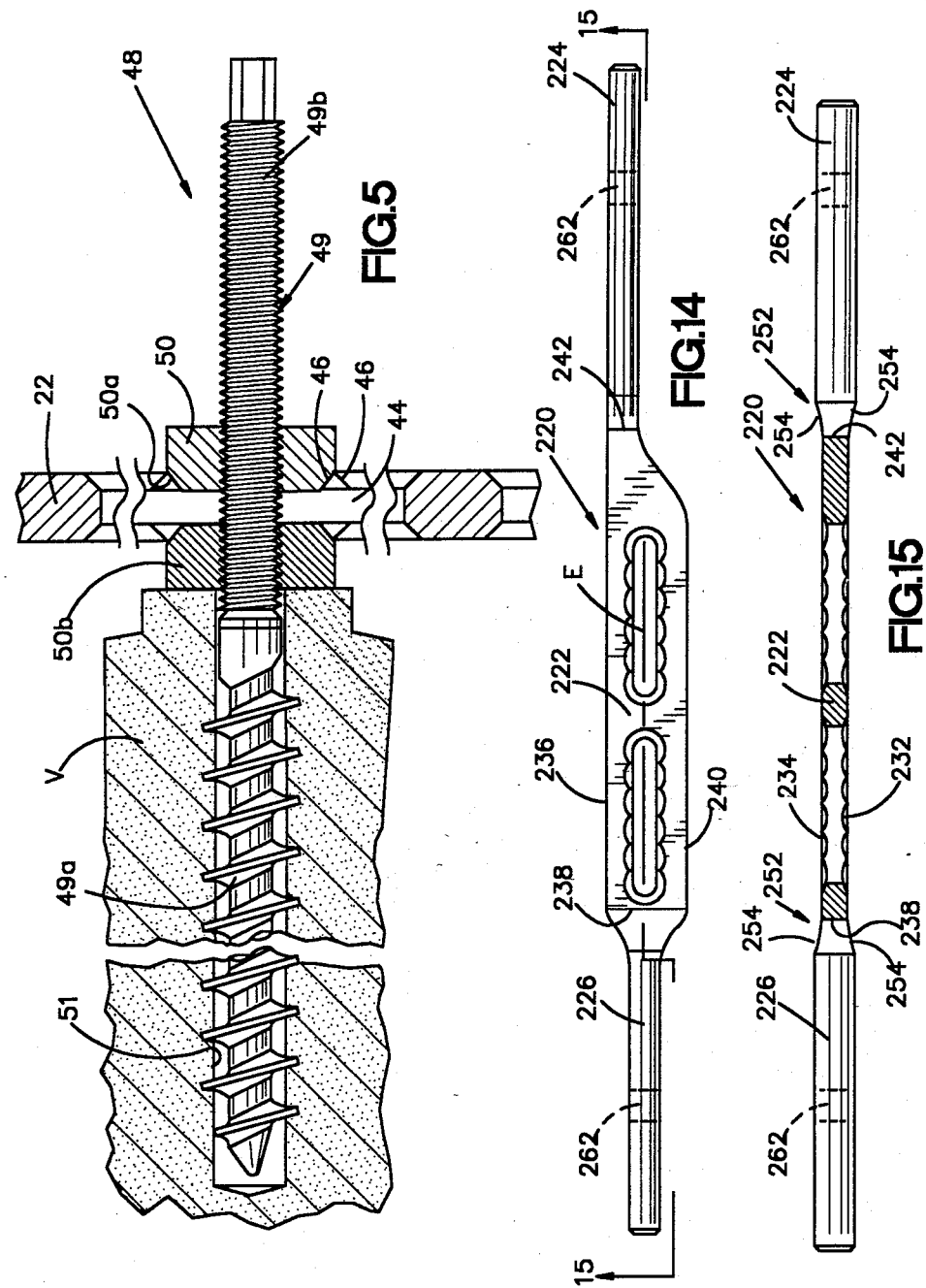

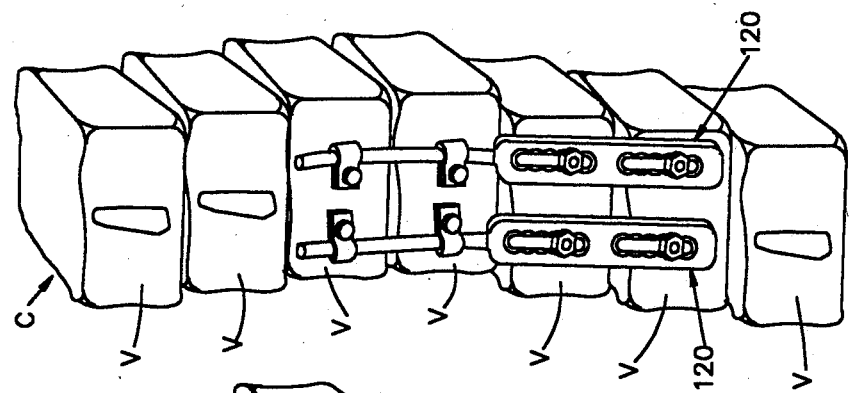
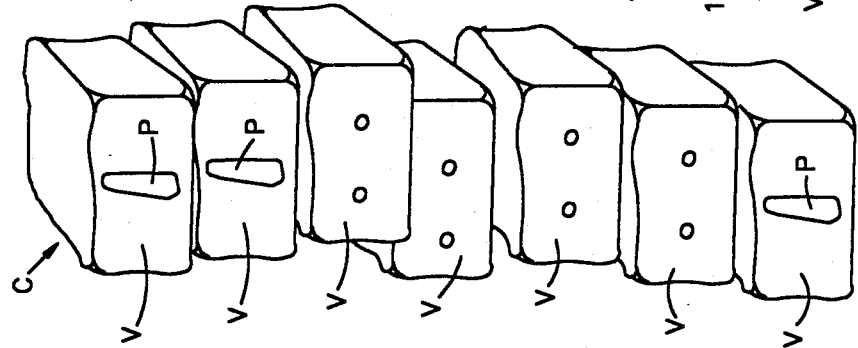
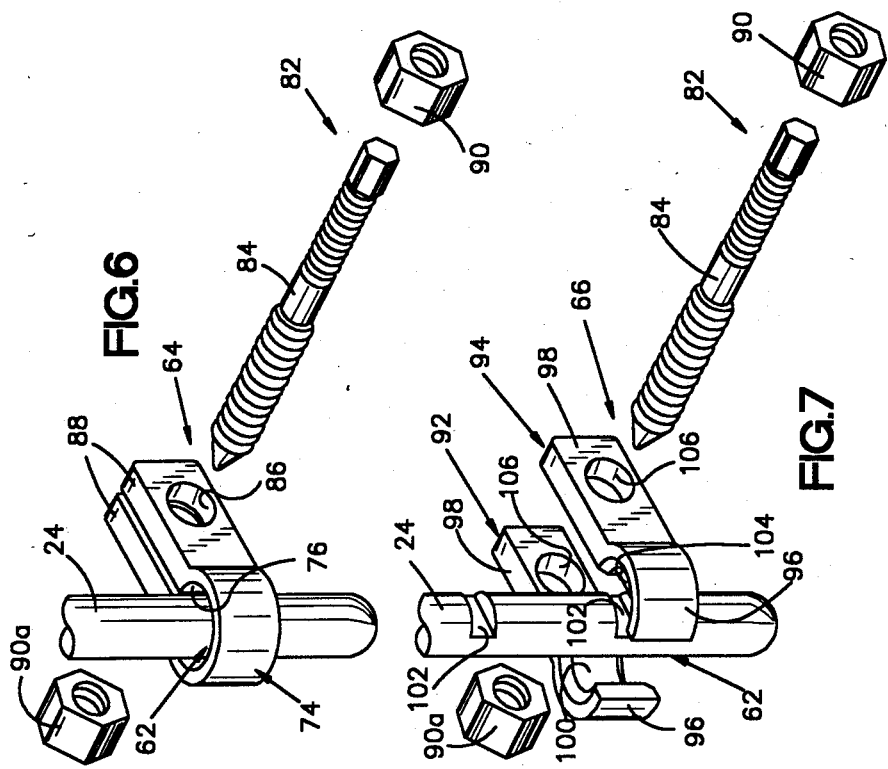

SURGICALLY IMPLANTABLE DEVICE FOR SPINAL COLUMNS

BACKGROUND OF THE INVENTION

1. Field of the Invention

The present invention relates to the surgical correction of spinal columns. Particularly, the present invention is a surgically implantable device connectable with spinal bodies of the spinal column for maintaining the relative positions of the spinal bodies.

2. Description of the Prior Art

It is known that the human spinal column is prone to deformation and degeneration. Deformation includes abnormal curvature of the spinal column, such as lordosis, kyphosis or scoliosis. Degeneration includes injury to, or failure of, the disc and ligaments located between adjacent spinal bodies of the spinal column. These conditions often require surgery to correct. During the surgical procedure, implantable devices are connected with the spinal bodies of the spinal column to correct the condition and to maintain the spinal bodies in a desired predetermined relationship.

Surgically implantable devices for the correction of spinal columns are known. U.S. Pat. No. 4,611,581 discloses one such implantable device in which a relatively rigid elongated plate is connectable with spinal bodies of the spinal column to maintain the spinal bodies in a desired relationship. However, the relatively rigid plate is not, as a practical matter, bendable to conform to a desired curvature of the spinal column. Furthermore, the bulk of the plate may preclude its use on some areas of the spinal column.

U.S. Pat. No. 4,648,388 discloses another type of implantable device in which a rod which is deformed by a surgeon to conform to a desired curvature of a spinal column. The rod is connected with spinal bodies of the spinal column to maintain the spinal bodies in a desired relationship and having a desired curvature.

U.S. Pat. No. 3,242,922 discloses another implantable device including a pair of plates which clamp the spinous processes of spinal bodies therebetween. The device also includes a pair of adjustable length rods. Each of the rods is pivotably connected at one end to a respective one of the plates. The other end of each of the rods is connectable with a patient's sacrum.

SUMMARY OF THE INVENTION

The present invention is a surgically implantable device for correcting and maintaining the relationship of spinal bodies of a spinal column. The surgically implantable device of the present invention provides a relatively rigid plate having at least one deformable rod fixedly connected to the plate and extending therefrom. The plate corrects and maintains the lateral relationship of spinal bodies and the rod is deformable to a desired curvature to maintain other spinal bodies in a desired lateral and dorsal relationship.

The apparatus of the present invention is a surgically implantable device for maintaining the relative positions of spinal bodies of the spinal column, such as the sacrum and vertebrae. The apparatus comprises a plate portion for connection with a first spinal body. The plate portion has a first major side surface for facing the first spinal body and a second major side surface. The plate portion has at least one opening extending through the first and second major side surfaces for receiving a fastener to connect the plate portion with the first spinal body. A first rod portion is fixedly connected to the plate portion and extends therefrom. The first rod portion is bendable to conform to a desired curvature of a portion of the spinal column. The first rod portion has a part for connection with a second spinal body.

The plate portion is elongated and has a longitudinal central axis. The opening in the plate portion is an elongated slot and has a longitudinal central axis extending in a direction parallel to the longitudinal central axis of the plate portion. The first rod portion extends from the plate portion in a direction parallel to the longitudinal central axis of the plate portion.

In one embodiment of the present invention, the first rod portion is offset from the longitudinal central axis of the plate portion. The surgically implantable device may be reversed so that the second major side surface of the plate faces the spinal bodies and the rod is displaced in the lateral direction. Thus, the surgeon has greater freedom in locating the fastener in the spinal body.

In another embodiment of the present invention, a second rod portion is fixedly connected to the plate portion and extends therefrom. The second rod portion extends in a direction parallel to the longitudinal central axis of the plate portion and opposite to the first rod portion. The second rod portion has a part for connection with a third spinal body. The second rod portion is also deformable to a desired curvature of a portion of the spinal column.

The first and second rod portions are fixedly connected to the plate portion at respective connecting portions. The connecting portions have relatively large blend radii extending between the respective rod portions and the plate portion for minimizing stress loading in the connecting portions.

BRIEF DESCRIPTION OF THE DRAWINGS

Further features of the present invention will become apparent to those skilled in the art to which the present invention relates from reading the following specification with reference to the accompanying drawings, in which:

FIG. 3 is an enlarged plan view of the device in FIG. 1;

FIG. 4 is a cross sectional view of the device of FIG. 3 taken approximately along line 4—4 in FIG. 3;

FIG. 5 is an enlarged cross sectional view of a portion of the device in FIG. 1 connected with a spinal body;

FIGS. 6 and 7 are perspective views of clamps for connecting a rod portion of the device with a spinal body;

FIG. 8 is an enlarged plan view of another embodiment of the device of the present invention;

FIG. 9 is a cross sectional view of the device in FIG. 8 taken approximately along line 9—9 in FIG. 8;

FIG. 10 is a schematic view of spinal bodies prepared for receiving the device of the present invention;

FIG. 11 is a schematic view of the device of FIG. 8 connected with spinal bodies of the spinal column;

FIG. 14 is an enlarged plan view of the device in FIGS. 12 and 13; and

FIG. 15 is a cross sectional view of the device in FIG. 14 taken approximately along line 15—15 in FIG. 14.

DESCRIPTION OF PREFERRED EMBODIMENTS

A pair of surgically implantable devices 20 (FIGS. 1 and 2), according to a first embodiment of the present invention, are connected with spinal bodies, such as a sacrum S and vertebrae V which make up a spinal column C. Each of the surgically implantable devices 20 is for correcting deformation and/or degeneration of the spinal column C and for maintaining the spinal bodies V, S in desired relative positions. The surgically implantable devices 20 are illustrated by way of example as being connected to lumbar vertebrae and the sacrum of the spinal column C. However, it will be apparent that the surgically implantable devices 20 may be used in other regions of the spinal column C, such as on the thoracic and/or cervical vertebrae. It will also be apparent that a single surgically implantable device 20 may be used to maintain the relative positions of the spinal bodies V, S.

Figures 1, 2:
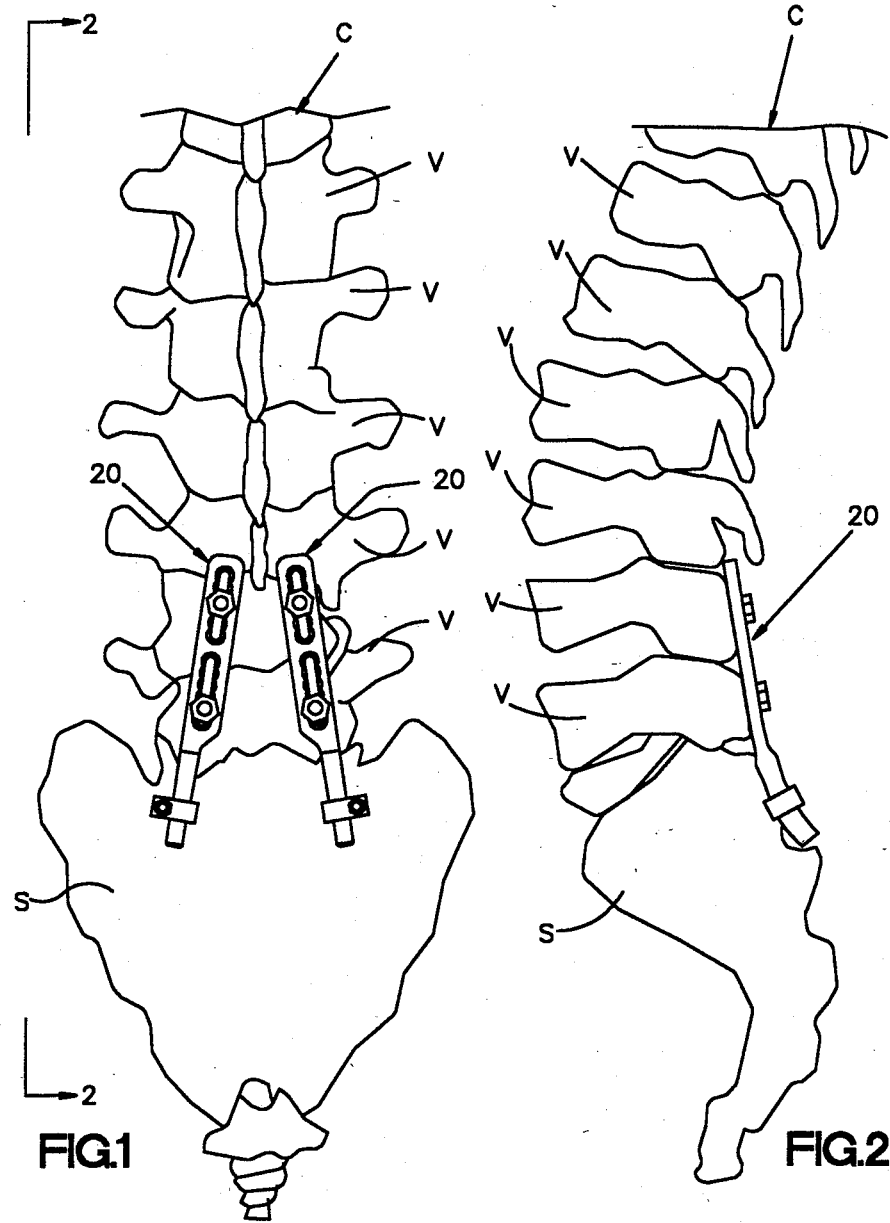
FIG. 1 is a view of one embodiment of the surgically implantable device, according to the present invention, connected to spinal bodies of a spinal column.
FIG. 2 is a view of the device in FIG. 1, taken approximately along line 2—2 in FIG. 1.

The surgically implantable device 20 (FIGS. 3 and 4) includes a plate portion 22 and a rod portion 24. The plate portion 22 is connectable with at least one spinal body V, as illustrated in FIG. 1. The plate portion 22 has a first major side surface 32 (FIG. 4) for facing the spinal bodies V when the plate portion is connected with a spinal body. The plate portion 22 also has a second major side surface 34 which extends in a direction generally parallel to the first major side surface 32. The plate portion 22 of the surgically implantable device 20 is elongated. That is, the major side surfaces 32, 34 have a length L which is larger than their width W. The major side surfaces 32, 34 are connected by a plurality of minor side surfaces 36, 38, 40, 42.

The plate portion 22 has a pair of openings or elongated slots 44 extending through the first and second major side surfaces 32, 34. The slots 44 receive a fastener 48 (FIG. 5) to connect the plate portion 22 with the spinal body V. The slots 44 provide for some adjustment or relocation of the plate portion 22 along the fastener 48 relative to the spinal bodies V during the surgical procedure. Each of the slots 44 (FIG. 3) have a longitudinal central axis A which extends in a direction parallel to the longitudinal central axis B of the plate portion 22, and preferably coaxially therewith. A plurality of recesses 46 are spaced along the length of each slot 44. The recesses 46 are located in both the first and second major side surfaces 32, 34 to permit the plate portion 22 to be reversed, or turned over, so that the second major side surface 34 faces the spinal bodies, as is described below.

The fastener 48 (FIG. 5) includes a screw 49 and a nut 50. The screw 49 has a first externally threaded portion 49a for threaded engagement with a surface defining an opening 51 in the spinal body V to connect the screw with the spinal body. The screw 49 also has a second externally threaded portion 49b for threaded engagement with the nut 50. When the nut 50 is threaded onto the second threaded portion 49b f the screw 49, it is drawn against the plate portion 22 of the surgically implantable device 20 to connect the plate portion with the spinal body V. One of the recesses 46 receives a portion 50a of the nut 50 to block sliding movement of the plate portion 22 relative to the screw 49 and, thus, the spinal body V.

Each of the recesses 46 is preferably frustoconical to match a frustoconical portion 50a of the nut 50 (FIG. 5). When the portion 50a of the nut 50 is seated in a recess 46, the plate portion 22 is prevented from sliding relative to the screw 49 when the screw 49 is connected with the spinal body V and the nut 50 is tightened against the plate portion. A spacer device, such as another nut 50b, is used on the screw 49 to space the plate portion 22 away from the spinal body V. While one type of fastener 48 is illustrated in FIG. 5, it will be apparent that other types of fasteners may be used.

The rod portion 24 of the surgically implantable device 20 is fixedly connected to the plate portion 22. The rod portion 24 extends from the minor side surface 42 of the plate portion 22. The rod portion 24 is connectable with the spinal body or sacrum S (FIG. 1) of the spinal column C. While the rod portion 24 is illustrated as connected to the sacrum S, it will be apparent that the rod portion could be located so it is connected with one of the vertebrae V.

The rod portion 24 has an elongated cylindrical configuration. The rod portion 24 is bendable or permanently deformable to conform to a desired curvature of the spinal column C. A hydraulic press located in the operating room is preferably used to deform the rod portion 24 to the desired curvature. The rod portion 24 may be deformed to incorporate a compound bend. That is, when the surgically implantable device 20 is connected with the spinal column C, the rod portion 24 is bent in the dorsal and the lateral planes. The plate portion 22 may be connected with the spinal column C before the rod portion 24 is connected therewith. Thus, the rod portion 24 can be restrained from moving by the plate portion 22 to aid installation. After the rod portion 24 is deformed, it is still rigid enough to maintain the spinal bodies V, S in a relationship which has a desired curvature.

A part 62 of the rod portion 24 is for connection with the spinal body S. FIGS. 6 and 7 illustrate clamps 64, 66, respectively, for connecting the part 62 of the rod portion 24 with the spinal body S. FIG. 6 illustrates a one-piece clamp 64 having a clamp portion 74 with an opening 76 which circumscribes and engages the part 62 of the rod portion 24. The part 62 of the rod portion 24 preferably has a knurled or roughened exterior surface.

A screw portion 84 of a fastener 82 is inserted through another opening 86 extending through leg portions 88 projecting from the clamp portion 74 and offset therefrom. The screw 84 is threaded into an opening in the spinal body S. The opening 86 extends in a direction generally perpendicular to the opening 76. When a nut 90 of the fastener 82 is tightened against the clamp 64, the leg portions 88 are drawn together and the clamp portion 74 grippingly engages the outer circumference of the part 62 of the rod portion 24 to connect the rod portion with the spinal body S. A second nut 90a is used to space the clamp 64 away from the spinal body V or S.

A two-piece clamp 66 is illustrated in FIG. 7. The clamp 66 has a pair of clamp halves 92, 94. Each of the clamp halves 92, 94 has a clamp portion 96 and a leg portion 98 extending therefrom. The clamp portions 96 define an opening 100 for circumscribing the part 62 of the rod portion 24. The part 62 of the rod portion 24 has a transverse slot 102 for receiving a nib 104 on the clamp half 94 to prevent rotational and axial movement of the rod portion relative to the clamp 66. The screw 84 of the fastener 82 is received in openings 106 in the leg portion 98 to connect the clamp 66 with the spinal body S. In FIG. 1, it will be seen that the fasteners 82 are located to the outside of the rod portions 24. This is merely for illustration purposes and it will be apparent that the surgeon may elect to locate the fasteners on the inside of the rod portions 24 for better securement to the sacrum S.

The rod portion 24, in the first embodiment of the present invention, is offset from the longitudinal central axis B of the plate portion 22. Thus, the surgeon may reverse, or turn over, the surgically implantable device 20 for optimal placement of the fasteners 48, 82 in the spinal bodies V, S. Since the plate portion 22 has recesses 46 in both major side surfaces 32, 34, the plate portion is blocked from sliding movement relative to the fastener 48. The end of rod portion 24 extending away from the plate portion 22 may be trimmed if necessary as may the ends of the screws 49, 84 extending beyond their respective nuts 50, 90.

The rod portion 24 and plate portion 22 are interconnected at a connecting portion 52. The connecting portion 52 has relatively large blend radii 54 extending between the connecting portion 52 and the plate portion 22, and between the connecting portion 52 and the rod portion 24. The relatively large blend radii 54 assure that stress loading in the connecting portion 52 is minimized.

FIGS. 8 and 9 illustrate a second embodiment of a surgically implantable device 120, according to the present invention. The surgically implantable device 120 is similar to the surgically implantable device 20 illustrated in FIGS. 3 and 4. The surgically implantable device 120 includes an elongated plate portion 122 and a rod portion 124. The plate portion 122 is connectable with a spinal body V or S. The plate portion 122 has first and second major side surfaces 132, 134, respectively, which extend generally parallel. The major side surfaces 132, 134 are interconnected by a plurality of minor side surfaces 136, 138, 140, 142.

The plate portion 122 includes a pair of longitudinally extending elongated slots 144. Recesses 146 are spaced along the slots 144 in only the second major side surface 134 of the plate portion 122 which faces away from the spinal bodies V, S of the spinal column C when the device 120 is connected with the spinal column. The rod portion 124 is fixedly connected to and extends from the minor side surface 142 of the plate portion.

The rod portion 124 extends from a central portion of the minor side surface 142 and is preferably coaxial with the longitudinal central axis D of the plate portion 122. The plate portion 122 of the second embodiment may be connected with a spinal body V or S of the spinal column C so the rod portion 124 disposed toward the sacrum S or the rod portion is disposed away from the sacrum, relative to the plate portion. The plate portion 122 has a part 162 which is connectable with the spinal body V or S.

The plate portion 122 and the rod portion 124 are interconnected at a connecting portion 152. The connecting portion 152 has relatively large blend radii 154 connecting the plate portion 122 with the connecting portion 152, and the connecting portion 152 with the rod portion 124. Thus, stress loading in the connecting portion 152 is minimized.

The spinal bodies V are schematically illustrated in FIG. 10 as blocks which have been prepared for receiving the surgically implantable device 120. The spinal bodies V which are to receive the device 120 have had the spinous process P removed. However, it will be apparent that the spinous process P may not have to be removed if the installation of the surgically implantable device 120 will not be affected by the spinous process. One of the spinal bodies $V_1$ is illustrated as being displaced laterally and dorsally from a normal or desired position in the spinal column C. It is this displacement that the present invention seeks to correct.

FIG. 11 illustrates the surgically implantable device 120, according to the second embodiment of the present invention, connected with spinal bodies V of the spinal column C. The rod portion 124 of the surgically implantable device 120 extends upwardly along the spinal column C, as viewed in FIG. 11, from the plate portion 122. The rod portion 124 has been bent by the surgeon during the surgical procedure in the dorsal plane to a desired curvature of the spinal column C. It will be apparent that the rod portion 124 could also be bent in the lateral plane as well. The clamps and fasteners used to connect the surgically implantable device 120 with the spinal bodies V are similar to those described above in the first embodiment and will not be described further.

Figures 12, 13:
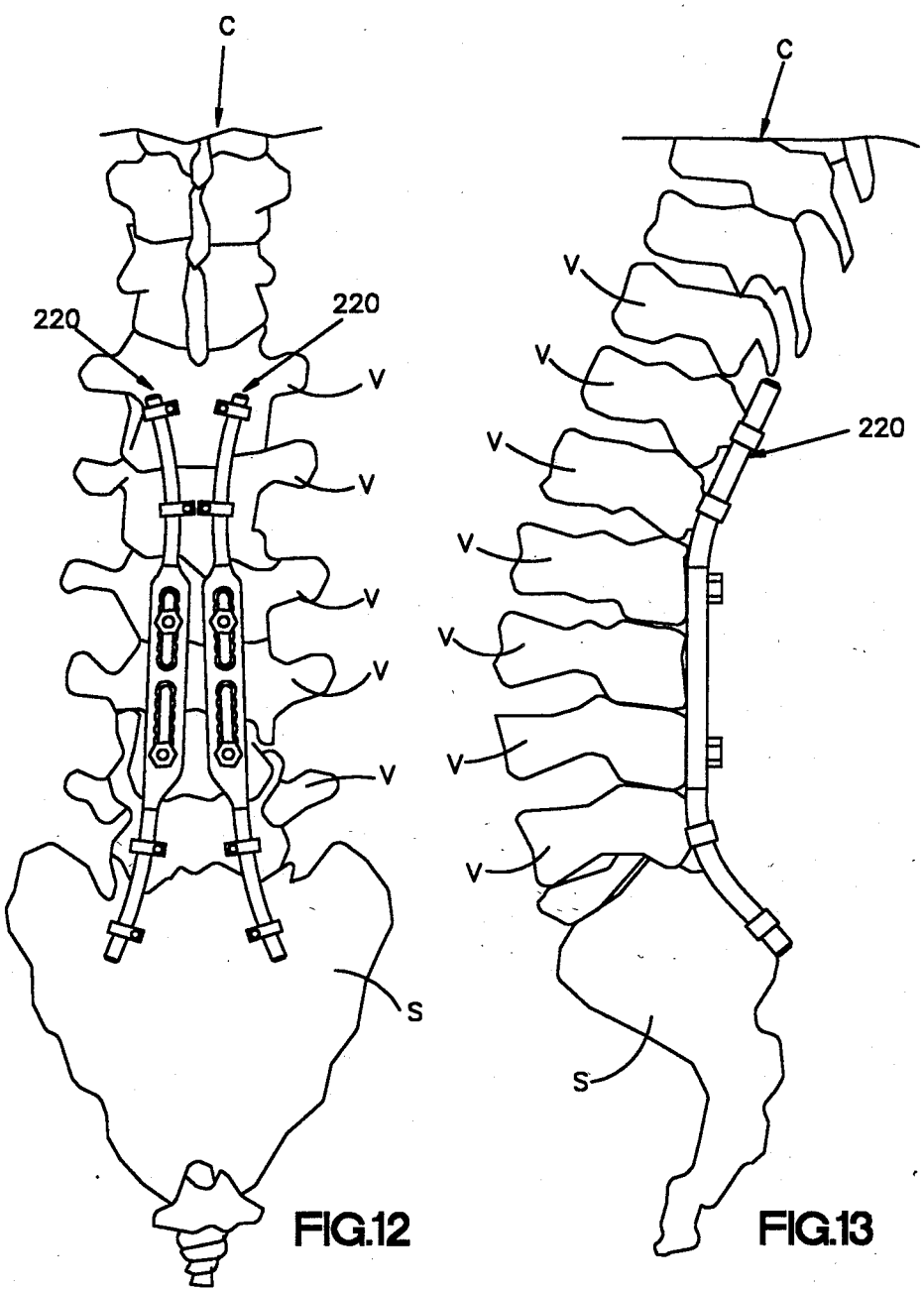
FIGS. 12 and 13 are views similar to FIGS. 1 and 2, of yet another embodiment of the device of the present invention connected with spinal bodies of the spinal column.

A third embodiment of the present invention is illustrated in FIGS. 12 and 13. A pair of surgically implantable devices 220 are connected with spinal bodies V, S of the spinal column C. The surgically implantable device 220 (FIGS. 14 and 15) includes a plate portion 222 and a pair of rod portions 224 and 226 fixedly connected to the plate portion. The rod portions 224, 226 extend generally parallel and in opposite directions from the plate portion 222. The rod portions 224, 226 extend in a direction parallel to the longitudinal central axis E of the plate portion 222. The plate portion 222 has major side surfaces 232, 234 interconnected by minor side surfaces 236, 238, 240, 242. The rod portion 224 extends from the minor side surface 242 of the plate portion 222. The rod portion 226 extends from the minor side surface 238. Each of the rod portions 224, 226 has a part 262 for connection with a spinal body V or S.

The plate portion 222 has a pair of elongated slots 244 extending through the major side surfaces 232, 234. The slots 244 have recesses 246 spaced therealong in both of the major side surfaces 232, 234. Thus, the surgeon may reverse the surgically implantable device 220 on the spinal column C so that fasteners connecting clamps with the rod portions 224, 226 are located optimally in a respective spinal body V, S.

The rod portion 224 is offset from the longitudinal central axis E of the plate portion 222. The rod portion 226 is located along the longitudinal central axis E of the plate portion 222. It will be obvious that both rod portions 224, 226 could be offset or both rod portions disposed along the longitudinal central axis E of the plate portion 222. The exact configuration and location of the rod portions 224, 226 will be dictated by the patient's requirements and selected by the surgeon during the preparation for the surgical procedure. The rod portions 224, 226 are deformable to conform to a desire curvature of a portion of the spinal column. The rod portions 224, 226 are illustrated in FIGS. 12 and 13 as having compound bends. That is, the rod portions are bent in the lateral and dorsal planes when the surgically implantable device 220 is connected with the spinal column C.

The plate portion 222 and the rod portions 224, 226 are interconnected at connecting portions 252. The connecting portions 252 have relatively large blend radii 254 connecting the plate portion 222 with one of the connecting portions 252, and the connecting portions 252 with the respective rod portions 224, 226. Thus, stress loading in the connecting portions 252 is minimized.

From the above description of a preferred embodiment of the invention, those skilled in the art will perceive improvements, changes and modifications. Such improvements, changes and modifications within the skill of the art are intended to be covered by the appended claims.

Having described a preferred embodiment of the invention, the following is claimed:

1. An apparatus for maintaining the relative positions of spinal bodies of a spinal column, said apparatus comprising:
   a plate for connection with a first spinal body, said plate having a central axis and having first and second major side surfaces at least one of which is for facing the first spinal body, said first and second major side surfaces extending substantially parallel to each other, and being interconnected by a plurality of minor side surfaces extending transverse to said first and second major side surfaces;
   surface means defining an opening extending through said plate between said first and second major side surfaces for receiving a fastener to connect said plate with the first spinal body;
   a first rod fixedly connected to and extending from one of said plurality of minor side surfaces of said plate and being connectable with a second spinal body, said first rod being deformable for the purpose of conforming to a desired curvature of a portion of the spinal column; and
   a connecting portion located between said first rod and said one minor side surface and having a transition zone of gradually changing cross section for minimizing stress loading in said connecting portion due to bending of said first rod.

2. The apparatus set forth in claim 1 wherein said first rod has a longitudinal central axis which extends coaxially with the central axis of said plate.

3. The apparatus set forth in claim 1 wherein said plate is elongate and the opening in said plate is elongate and extends in a direction substantially parallel to the central axis of said plate and further including surface means defining a plurality of recesses in said second major side surface of said plate spaced along the length of the opening, one of said plurality of recesses for receiving a portion of the fastener to block sliding movement of said plate relative to the fastener.

4. The apparatus set forth in claim 1 further including a second rod fixedly connected to and extending from another minor side surface of said plate in a direction substantially parallel to the central axis of said plate and opposite to said first rod, said second rod being connectable with a third spinal body and being deformable for the purpose of conforming to a desired curvature of another portion of the spinal column.

5. The apparatus set forth in claim 1 further including clamp means for connecting said first rod with the second spinal body, said clamp means comprising a member having surfaces circumscribing a portion of said first rod and a leg extending from said member, said leg having an opening offset from said member for receiving another fastener to connect said clamp means to the second spinal body.

6. The apparatus as set forth in claim 1 wherein said first rod has a longitudinal central axis which is spaced apart from and extends parallel with the central axis of said plate, and wherein each of said major side surfaces is for facing the first spinal body.

7. The apparatus as set forth in claim 1 wherein each of said major side surfaces is for facing the first spinal body, and wherein said plate is elongate and the opening in said plate is elongate and extends in a direction substantially parallel to the central axis of said plate and further includes first surface means defining a plurality of recesses in said first major side surface of said plate spaced along the length of the opening and second surface means defining a second plurality of recesses in said second major side surface of said plate spaced along the length of the opening, one recess of said first and second plurality of recesses for receiving a portion of the fastener to block sliding movement of said plate relative to the fastener.

* * * * *